US011259928B2

(12) United States Patent
Lee

(10) Patent No.: US 11,259,928 B2
(45) Date of Patent: Mar. 1, 2022

(54) HYBRID HEART VALVE FUNCTION TESTER SPECIFICALLY DESIGNED FOR PRODUCTION EVALUATION OF PROSTHETIC HEART VALVE PRODUCTS

(71) Applicant: Shouyan Lee, Irvine, CA (US)

(72) Inventor: Shouyan Lee, Irvine, CA (US)

(*) Notice: Subject to any disclaimer, the term of this patent is extended or adjusted under 35 U.S.C. 154(b) by 172 days.

(21) Appl. No.: 16/534,958

(22) Filed: Aug. 7, 2019

(65) Prior Publication Data

US 2020/0046500 A1 Feb. 13, 2020

Related U.S. Application Data

(60) Provisional application No. 62/715,683, filed on Aug. 7, 2018.

(51) Int. Cl.
*A61F 2/24* (2006.01)
*G01M 13/003* (2019.01)

(52) U.S. Cl.
CPC ......... *A61F 2/2472* (2013.01); *G01M 13/003* (2019.01)

(58) Field of Classification Search
CPC .......................... A61F 2/2472; G09B 23/303
See application file for complete search history.

(56) References Cited

U.S. PATENT DOCUMENTS

| 5,284,423 A | * | 2/1994 | Holdsworth | G09B 23/28 417/28 |
| 5,531,094 A | * | 7/1996 | More | A61F 2/2472 73/1.72 |
| 5,769,615 A | * | 6/1998 | Giter | F04B 13/00 417/415 |
| 5,916,800 A | | 6/1999 | Elizondo | |

(Continued)

OTHER PUBLICATIONS

International Search Report for the corresponding PCT application PCT/US2019/045578 dated Oct. 7, 2019.

(Continued)

*Primary Examiner* — Paul M. West
*Assistant Examiner* — Mark A Shabman
(74) *Attorney, Agent, or Firm* — WPAT Law, P.C.; Anthony King

(57) ABSTRACT

A multifunctional prosthetic heart valve tester having a circuit of fluid channels, wherein the circuit has a main loop of fluid channel capable of providing a first flow path for a testing fluid. There can be a first branch-off point on the main loop having a first branch channel branching off and fluidly connecting the main loop to a three-way connection. There is a second branch-off point on the main loop having a second branch channel branching off and fluidly connecting the main loop to the three-way connection. A third branch-off point is provided on the main loop having a third branch channel branching off and fluidly connecting the main loop to the three-way connection. There is linear motor and a steady-flow pump disposed on the circuit. Wherein selective shut off of certain channels and selective on/off of the linear motor/steady flow pump allows the device to test the prosthetic valve in the following modes: the steady forward flow mode, steady backward flow mode, pulsatile mode, and hybrid mode.

17 Claims, 8 Drawing Sheets

(56) References Cited

U.S. PATENT DOCUMENTS

| | | | |
|---|---|---|---|
| 6,062,075 A * | 5/2000 | Ritz | A61F 2/2472 607/119 |
| 2002/0116054 A1 | 8/2002 | Lundell et al. | |
| 2003/0066338 A1* | 4/2003 | Michalsky | A61F 2/2472 73/37 |
| 2010/0004740 A1* | 1/2010 | Seguin | A61F 2/2433 623/2.18 |
| 2011/0217684 A1 | 9/2011 | Park et al. | |
| 2014/0099620 A1* | 4/2014 | Lee | G09B 23/30 434/268 |
| 2016/0045312 A1* | 2/2016 | Braido | A61B 5/026 623/2.37 |
| 2018/0274689 A1* | 9/2018 | Gagne | F16K 7/06 |

OTHER PUBLICATIONS

Written Opinion from International Search Authority for the corresponding PCT application PCT/US2019/045578 dated Oct. 7, 2019.

* cited by examiner

HYBRID HEART VALVE FUNCTION TESTER SPECIFICALLY DESIGNED FOR PRODUCTION EVALUATION OF PROSTHETIC HEART VALVE PRODUCTS

CROSS-REFERENCE TO RELATED APPLICATIONS

This application claims priority to, U.S. Provisional Pat. No. 62/715,683, filed on Aug. 7, 2018, hereby incorporated by reference in its entirety.

FIELD OF THE DISCLOSURE

The present disclosure relates generally to prosthetic valve simulators and testers, and more particularly to a portable multifunction tester and simulator for prosthetic heart valves.

BACKGROUND

The advent of the prosthetic heart valve has provided many patients with both improved quality of life and increased longevity. The primary function of a prosthetic heart valve is to act as a check valve, opening to permit antegrade blood flow and closing to prevent retrograde flow, about one hundred thousand times a day. The valve elements move in response to a threshold pressure gradient in one direction, allowing flow through the valves, while closing in the opposite direction, preventing reverse flow below the threshold pressure gradient.

Prosthetic heart valves go through extensive testing and quality checks because failure of the valves in vivo can have catastrophic results. Certain characteristics such as durability, and proper fluid flow, are rigorously tested before a valve is deemed fit.

Evaluation of prosthetic heart valve on a production line is critical for quality assurance and improvement of valve manufacturing process Therefore, there is an apparent need for a simple and compact system that facilitates multiple testing modes.

SUMMARY OF THE DISCLOSURE

Embodiments of the present disclosure are directed to a testing system and method. One such embodiment describes a prosthetic valve testing system including a solid housing having a main channel defining a circuitous flow pattern for a fluid. The solid housing can include a linear motor in flow communication with the main channel, including a piston. The piston moves in a reciprocating motion to apply a pulsating component to the fluid dynamics. Further, there can be a holding mechanism for holding a prosthetic valve in the main channel.

Another embodiment of the present disclosure describes the main channel having three branch-off points, each of which has a branch channel that converge at a three-way connection. In one embodiment, there can be a three-way valve at the three-way connection for a user to selective control the flow of fluid in these three branch channels.

In other embodiments, the tester can have a compliance module, a flow resistance, a fluid reservoir, and a number of mechanical valves. There can also be a number of sensors, readers, and other measuring means to help collect data.

In yet another embodiment, there can be a steady flow pump in the circuit to provide a steady motion of flow in the circuit as opposed to the pulsatile motion provided by the linear motor. In one embodiment, both the steady flow pump and the linear motor are used simultaneously.

In still other contemplated embodiments, the selective shut off of certain channels and selective use of the linear motor and steady flow pump allow the device to test the prosthetic valve in various modes: the steady forward flow mode, steady backward flow mode, pulsatile mode, and hybrid mode.

Ideal method for production evaluation sought after the following characteristics: simple and easy to operate, good repeatability of the parameters to measure, covers all critical valve performance indicators, easy to clean and maintain sterile, and minimize the possibility of contamination. It has been challenging because the normal in-vitro testing as required by ISO 5840 are usually not suitable for production use; either the test is simple but does not cover the critical valve performance (such as the steady flow tests), or difficult to operate and to obtain repeatable parameter (such as hydrodynamic test).

This disclosure reveals a hybrid apparatus/method to evaluate prosthetic heart valves on production line, which uses parameter repeatability of steady flow test and the physiological similarity of a pulse duplicator to record valve opening/closing plus accurate pressure gradients and leakage measurement. In some embodiments, the system can use all biocompatible/serializable materials.

In another objective, contemplated embodiments can also include a top loading valve mounting mechanism to assure minimal fluid loss for least possibility of contamination.

Other aspects and features of the present disclosure will become apparent from the following detailed written description of the preferred embodiments and aspects taken in conjunction with the following drawings, although variations and modifications thereto may be effected without departing from the spirit and scope of the novel concepts of the disclosure.

BRIEF DESCRIPTION OF THE DRAWINGS

The accompanying drawings illustrate one or more embodiments and/or aspects of the disclosure and, together with the written description, serve to explain the principles of the disclosure. Wherever possible, the same reference numbers are used throughout the drawings to refer to the same or like elements of an embodiment. The drawings are illustrative in nature and are not necessarily drawn to scale.

DETAILED DESCRIPTION

Figure 1:
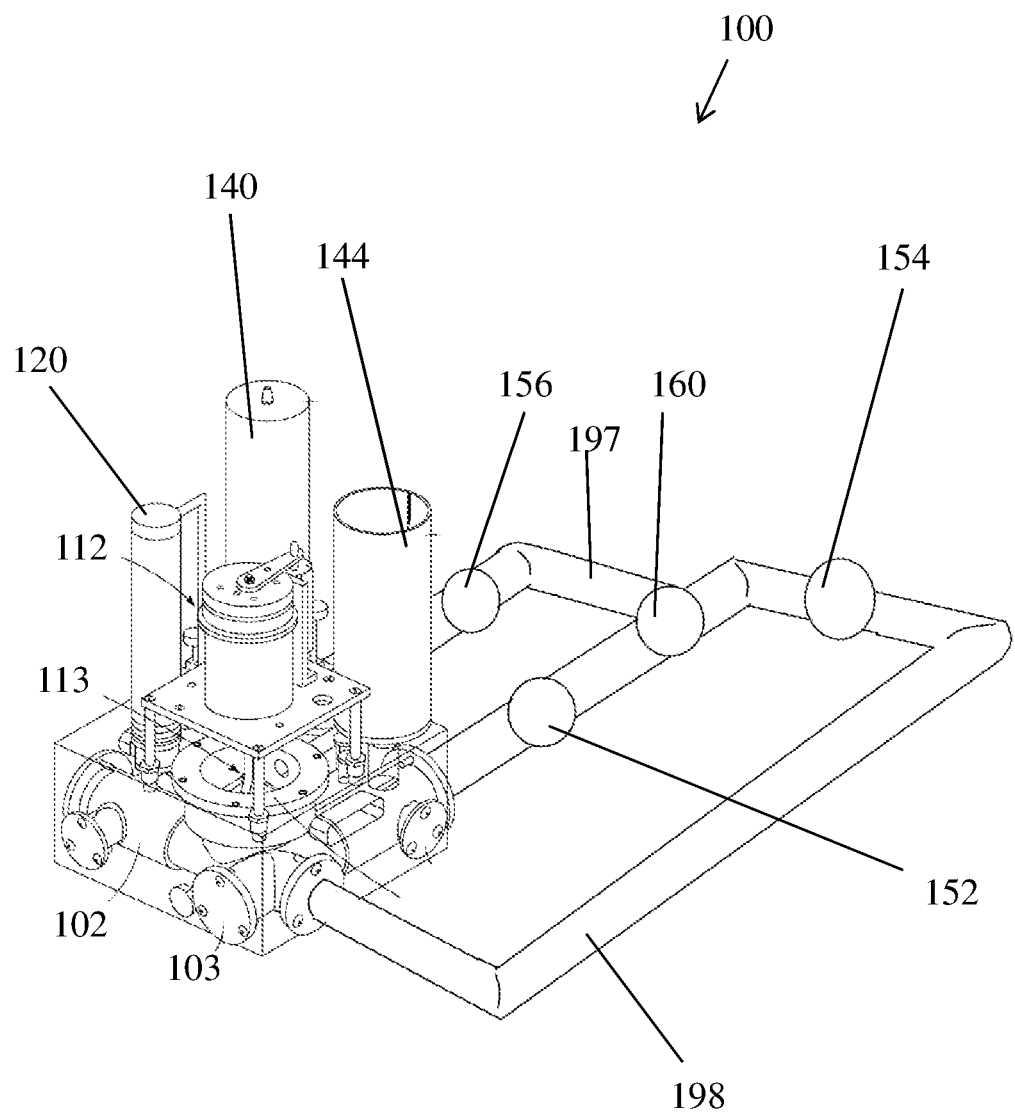
FIG. 1 illustrates a perspective view of the contemplated prosthetic valve testing system according to one embodiment of the present disclosure.

To promote an understanding of the principles of the present disclosure, reference will now be made to the embodiments illustrated in the drawings and specific language will be used to describe the same. It will, nevertheless, be understood that no limitation of the scope of the disclosure is thereby intended; any alterations and further modifications of the described or illustrated embodiments and any further applications of the principles of the disclosure as illustrated therein are contemplated as would normally occur to one skilled in the art to which the disclosure relates. All limitations of scope should be determined in accordance with and as expressed in the claims.

Overview

The tester system 100 can be a combination of a compact pulse duplicator (as disclosed in U.S. Pat. No. 8,800,348, which is incorporated herein by reference in its entirety) and a DC controlled pump and orifice loop 150. Embodiments of the present disclosure describe a compact system for testing a prosthetic valve.

Referring now to FIG. 1, a tester 100 is shown. The tester 100 can have a number of conduits 102 linked together to for a circuit of channels where testing fluid may flow. Similar to the tester in U.S. Pat. No. 8,800,348, there can be a solid block of transparent material having conduits 102 provided therein. The transparency of the material allows a user to observe the fluids conveniently.

In essence, the solid transparent block is the pulse duplicator portion 110. The pulse duplicator portion has a linear motor 112, a valve testing unit 120, a compliance module 140, a fluid reservoir 144, all of which are fluidly connected by a main channel. This main channel can also be described as having a circuitous flow path.

The contemplated linear motor unit 112 includes a piston 113 and a rolling diaphragm. The linear motor unit 112 can be used to generate a pulsatile flow of physiologically relevant conditions.

In valve testing unit 120, pressure gradient across the valve can be optionally measured. The disclosed compliance module 140 and resistance can be the same compliance and resistance used in a typical pulse duplicator, such as those disclosed in U.S. Pat. No. 8,800,348.

As will be described later, the reservoir 144 can have a lid and can have an open top exposing the fluid to the atmosphere. The open top allows easy filling of fluid. There can be a mechanical valve disposed between reservoir 144 and the linear motor unit 112 for purposes which will be explained later.

In the embodiment where a transparent block is used, because the conduits are created by first burrowing through the block, the ends of the through channel are capped off with an end cap 103 so that fluid is kept in the circuit of channels.

In some embodiments, the vertical reciprocating motion of the piston 113 simulates a heart's pumping function. As piston 113 reciprocates, the fluid flows through the main channel which holds the prosthetic valve. There can optionally be a heating rod positioned within the system to increase the temperature of the fluid, as desired. For proof testing, the system employs a set of sensors to monitor the prosthetic valves and collect other data.

Figure 2:
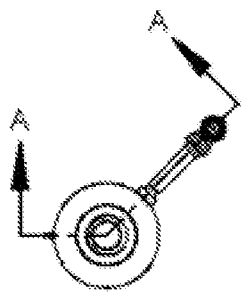
FIG. 2 is a top view of the valve testing unit according to one embodiment of the present disclosure.
Figure 3:
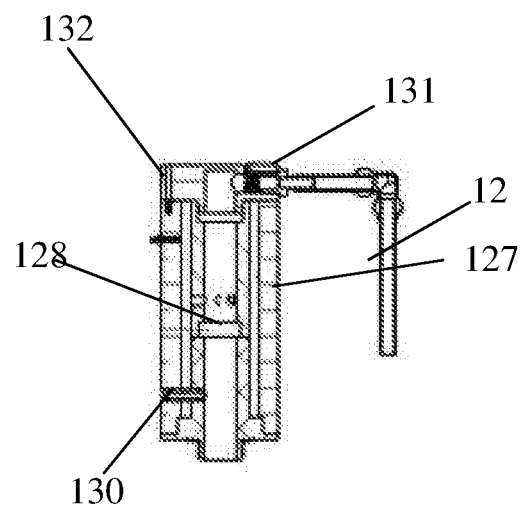
FIG. 3 illustrates cross-sectional view taken from line A-A of FIG. 2.
Figure 4:
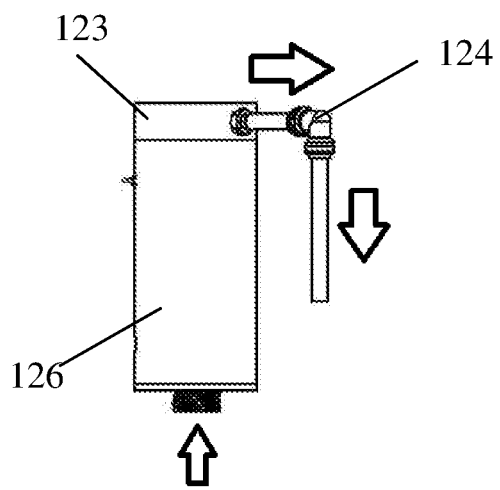
FIG. 4 illustrates an exemplary valve testing unit of FIG. 2.

The pulse duplicator portion 110 will be described in more details in FIGS. 2-4. In FIG. 2, the top of the valve testing unit 120 is shown. FIG. 3 is the cross-sectional view taken along line A-A in FIG. 2. In one embodiment, This design has a feature of loading the test valve from the top of the tester 100 (as opposed to side-loading as shown in U.S. Pat. No. 8,800,348). In this way, there is no need to drain the testing fluid from the assembly between valve testings. It serves to simplify testing procedure and reduces possibility for contamination from draining and refilling testing fluid.

The mounting assembly 123, when disconnected from a quick disconnect fitting 124, the entire assembly with test valve (encased within the assembly) can be topside removed from the tester base 126. There can be a valve adaptor 127 with a valve mounting space 128 attached to the mounting piece 129, and can be customizable based on various valve designs/sizes. There can additionally be two pressure ports 130, 131 that are used to measure the upstream and downstream pressures of the test valve, thus to obtain the pressure gradient measurements.

The valve testing unit 120 can screw onto the transparent block housing and directly connect with the main loop of channel in the transparent block. The directly of fluid flow is shown by the arrows in FIG. 4. It should be noted that the fluid must travel through the valve testing unit 120 because the travel path as shown in FIG. 4 is part of the main loop of channel and the testing fluid must pass through the valve testing unit 120 in order to keep the circuitous flow as intended.

Again, the forward flow direction is from bottom of the valve test unit 120 (see arrows in FIG. 4) flowing through the testing valve on the mounting assembly 123, and out through the smaller conduit where the quick connect 124 is located. The smaller conduit is fluidly connected to the main fluid loop of the compact pulse duplicator. In other words, in a forward flow direction, fluid from the main loop first enters the valve test unit 120 following the arrows shown in FIG. 4, passes through the test valve, and through the smaller conduit, and back into the main fluid loop.

When the valve is to be replaced, the bolt 132 or other locking mechanisms is released, the quick disconnect 124 is unplugged, the mounting assembly 123 is then removed from the tester base 126. The valve can be replaced by replacing the valve adaptor 127 with a new adaptor having a new test valve, or removing the test valve from the mounting assembly 123. Then, the new valve can be inserted in mounting space 128, or a valve adaptor 127 with a new test valve.

In one embodiment, the reservoir 144 can have an adjusted fluid height relative to the valve testing unit 120 so as to prevent fluid overflow during valve replacement. In another embodiment, the reservoir 144 is higher than the valve testing unit 120. In yet another embodiment, the reservoir 144 is lower than the valve testing unit 120.

There can optionally be a transparent window at the top of the valve test unit 120 so that the valve motion/shape can be observed and recorded.

Exemplary Embodiments

Figure 5:
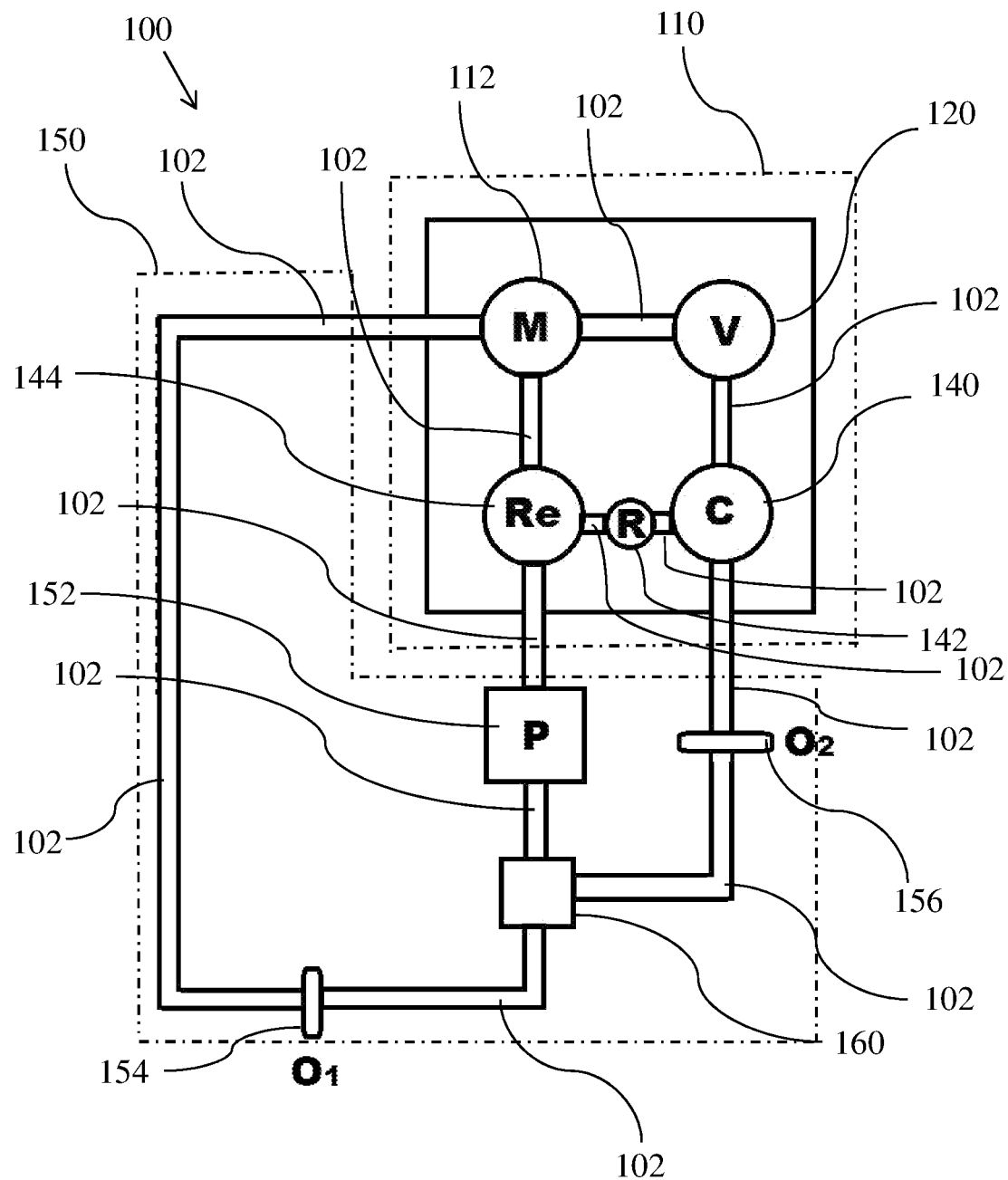
FIG. 5 illustrates a flow path diagram having various components according to one embodiment of the present disclosure.

FIG. 5 illustrates an exemplary testing system 100 that is capable of performing multiple testing modes. The system 100 includes a pulse duplicator portion 110 as described above, and a pump and orifice loop portion 150 as will be described below. The housing of the pulse duplicator portion 110 can be a solid transparent block made of acrylic, polycarbonate, or other suitable material. A main channel can be drilled into the housing and subsequently, the openings on the outer surface are covered using end caps 103. Once the openings are covered, the main channels provides a closed loop path for fluid flow within the housing. It should be understood that any desired flow channel design may be drilled into this solid housing.

Although the disclosed embodiment is manufactured by drilling four straight channels (that intersects with each other) into a solid transparent block of acrylic material, one skilled in the art would appreciate other suitable synthetic or natural polymeric material can also be used. One skilled in the art would also appreciate the channels can be created by other means known in the manufacturing art. For example, one may create the housing (having internal channels) by injection molding, or by 3-D printing. Further, the housing does not have to be a solid piece of material. For example, the channel 104 can be transparent pipes and tubing installed inside of a transparent hollow housing.

The main channel is generally a cylindrical hollow passage that forms a circuitous flow pattern for any fluid.

Figure 10:
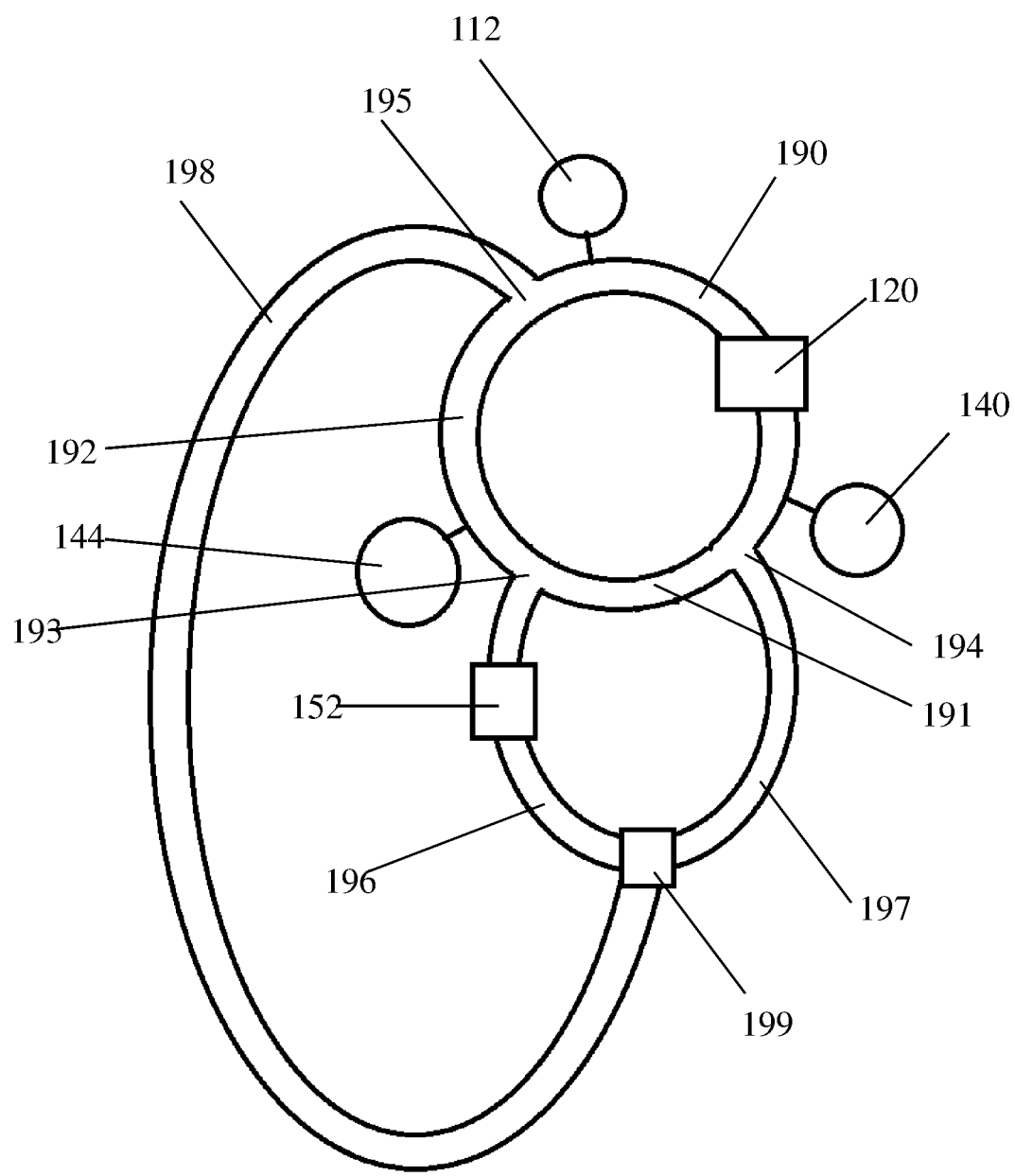
FIG. 10 illustrates the system in a simplified flow diagram according to one embodiment of the present disclosure.

It should be particularly noted that the compliance module 140 does not necessarily require three conduits 102 leading into it. In most embodiments, the compliance module is a branching off of the main loop of channel at or near the second branching-off point 194 (as shown in FIG. 10). Similarly, the reservoir 144 does not necessarily require three conduits 102 leading into it as FIG. 5 might seem to suggest. In most embodiments, the reservoir is a branching off of the main loop of channel at or near the first branching-off point 193 (as shown in FIG. 10).

There can be a steady flow pump 152. In one embodiment, the steady flow pump 152 can only pump the fluid in one direction, for example, in the direction towards the bottom of the page in FIG. 5.

Steady Forward Flow Mode

Figure 6:
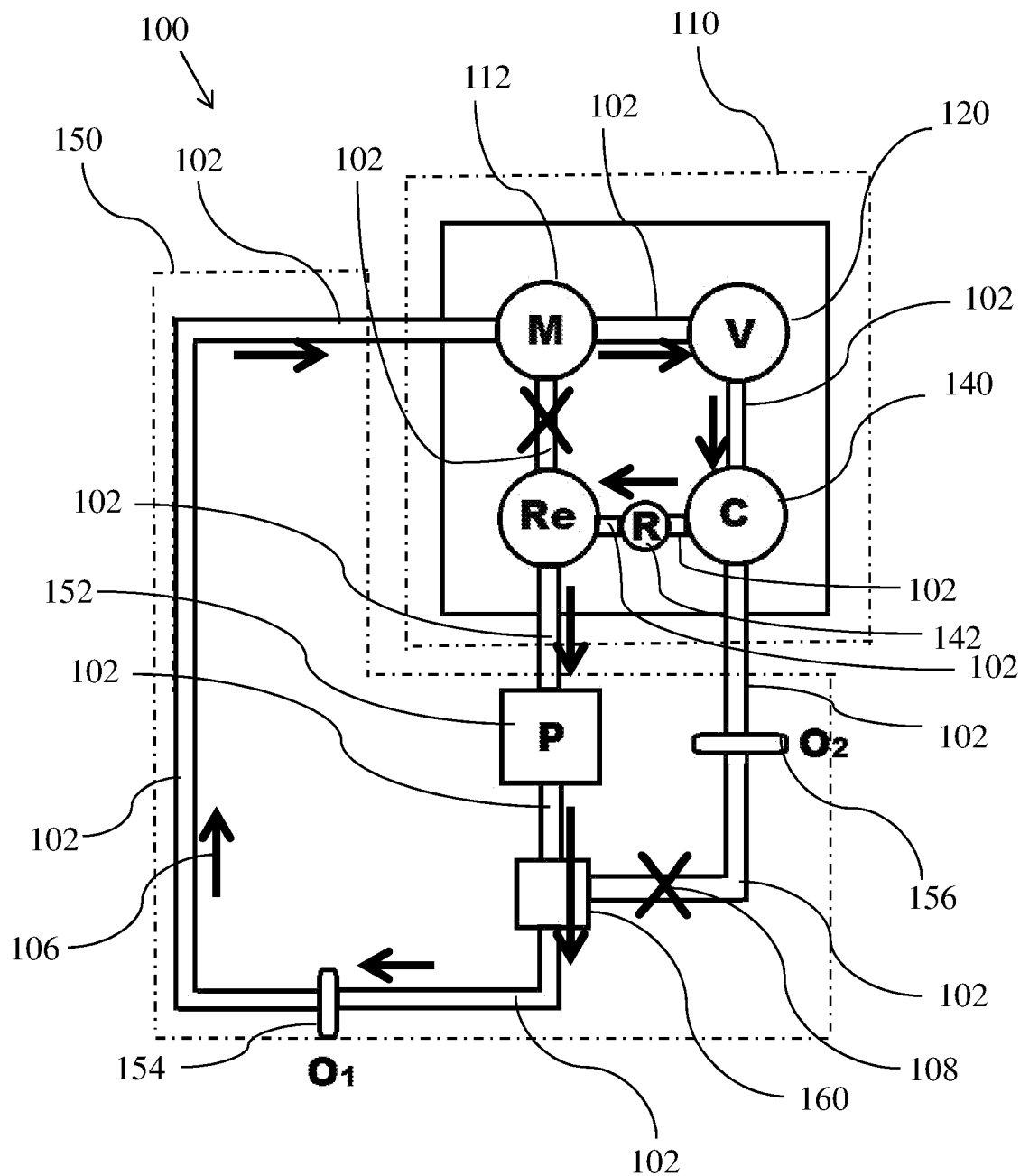
FIG. 6 illustrates the system of FIG. 5 now being used for steady forward flow testing according to one embodiment of the present disclosure.

Referring now to FIG. 6, using the components shown in FIG. 5, the tester 100 can be set up for steady forward flow test in the following ways: fluid is pumped through the designated loop in a steady flow by steady flow pump 152. Only the steady flow pump 152 is turned on, The fluid loop of this mode is connected as shown in FIG. 6 by switching the 3-way valve 160 such that flow is directed from the steady flow pump 152 to orifice one 154, and not to orifice two 156. Also, flow from the reservoir 144 to the linear motor 112 is shut off by a mechanical valve. The steady flow pump 152 is to generate a given flow rate controlled by the flowmeter measurement (collected by orifice one 154 flowmeter), then the pressure drop across the open test valve is measured at the valve section. This mode will provide an accurate assessment of valve effective orifice area (EOA). The valve opening shape can be observed/recorded at the valve section.

Steady Backward Flow Mode

Figure 7:
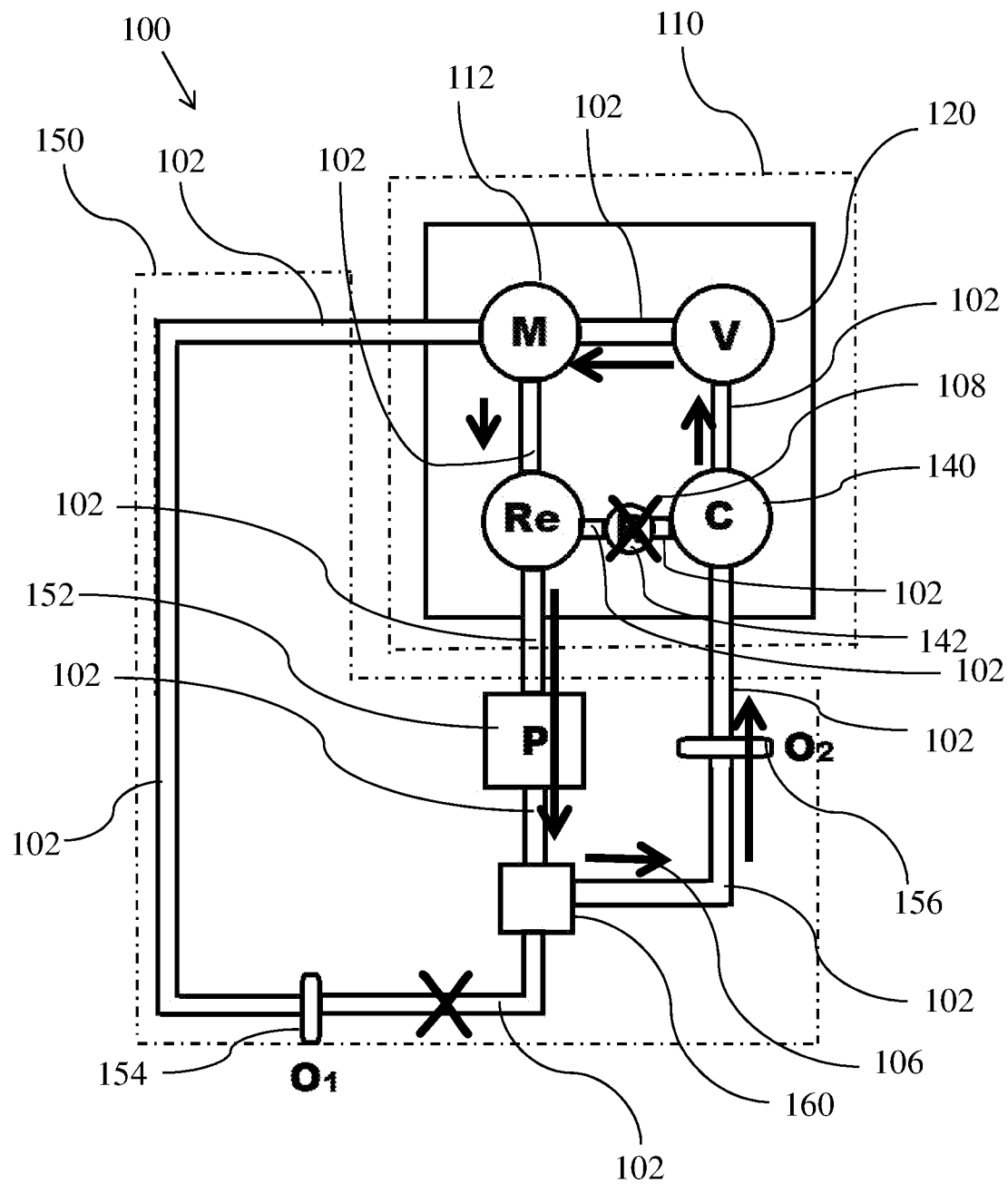
FIG. 7 illustrates the system of FIG. 5 now being used for steady backward flow testing according to one embodiment of the present disclosure.
Figure 8:
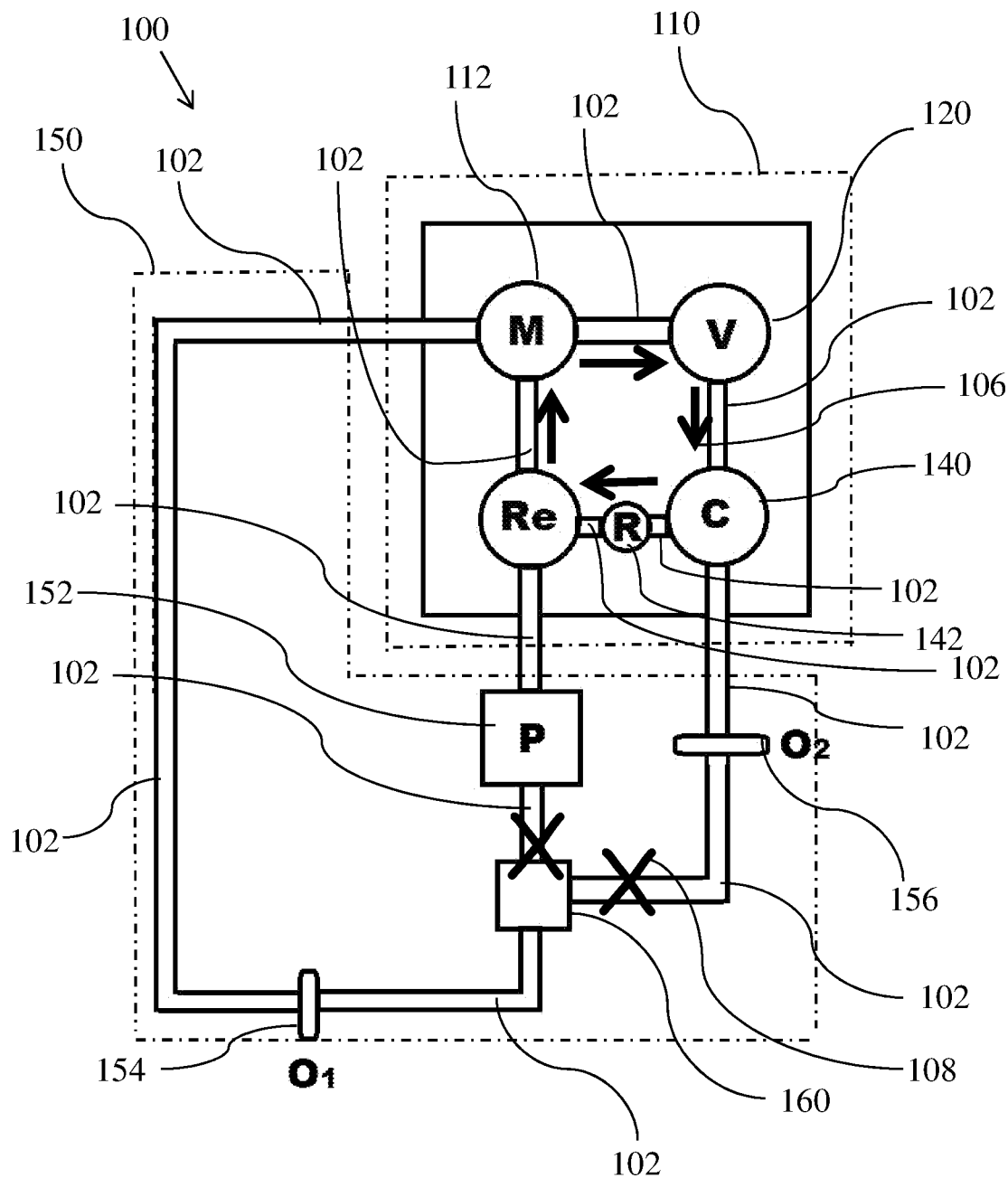
FIG. 8 illustrates the system of FIG. 5 now being used for pulsatile testing according to one embodiment of the present disclosure.
Figure 9:
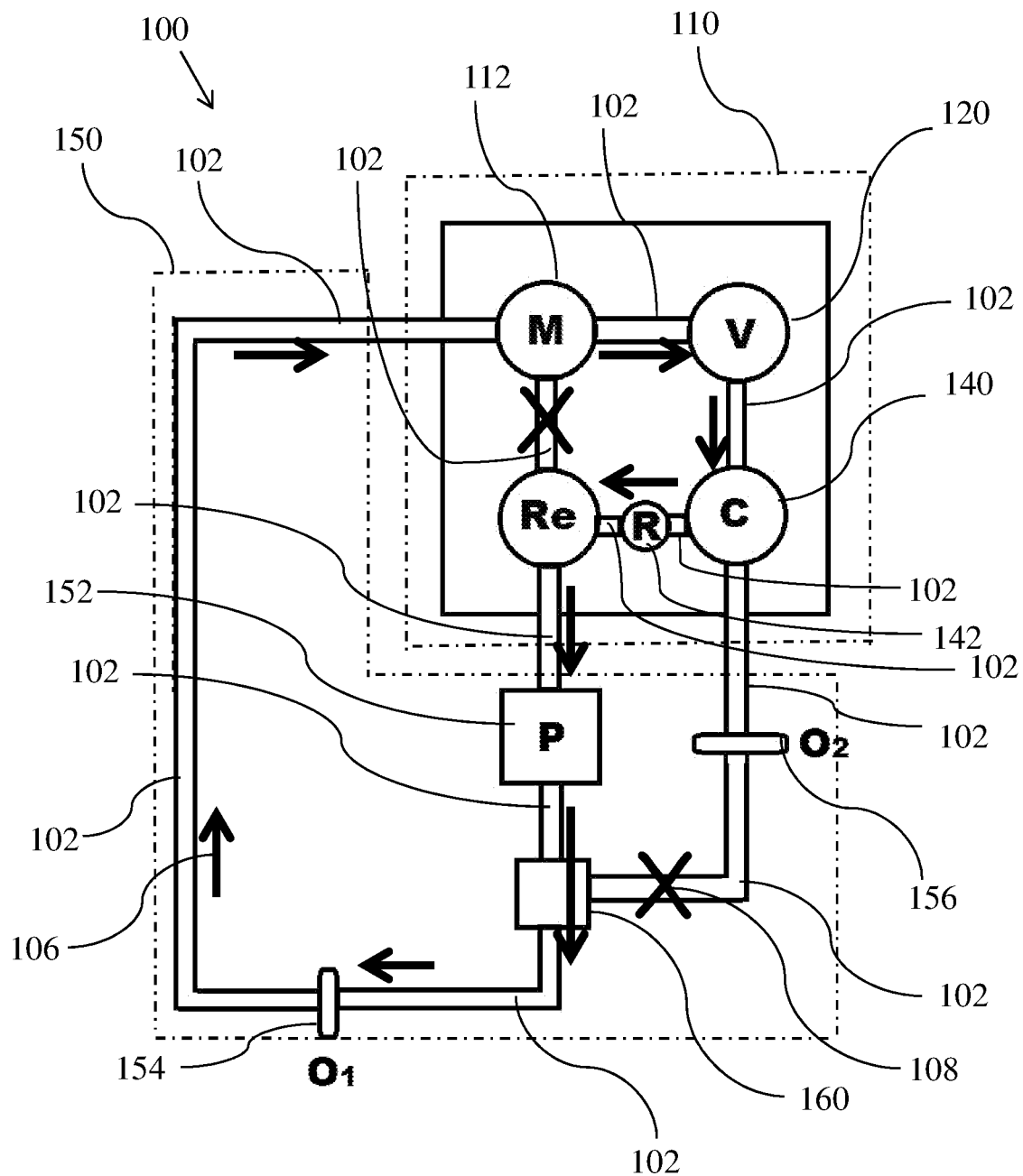
FIG. 9 illustrates the system of FIG. 5 now being used for hybrid testing according to one embodiment of the present disclosure.

In this mode, using the components shown in FIG. 5, the tester 100 can be set up for steady backward flow test in the following ways: fluid is pumped through the designated loop in a steady flow by steady flow pump 152. Only the steady flow pump 152 is turned on, the fluid loop is connected as in FIG. 7 by switching the 3-way valve so as to direct the flow from steady flow pump 152 to orifice two 156 and not to orifice one 154. This can be used to test a leakage of the test valve. The pump is then to generate a given pressure drop across the closed test valve, the leakage flow is then measured through the leakage flow meter at orifice two 156.

Here, the direct connection between reservoir 144 and the compliance module 140 is shut off. The closing configuration of the valve and the shape can be observed and recorded at the valve section through a transparent viewing window.

Pulsatile Flow Mode

When the steady flow pump 152 is turned off, and the 3-way valve 160 shuts off any flow towards the pump and orifice loop 150, now no fluid flow is directed to pass through orifice one 154 and orifice two 156. Physiologically relevant flows and pressures can be generated so the valve opening and closing kinematics can be observed at the valve section.

Hybrid Mode

During the steady forward flow mode described above in FIG. 6, the linear motor 112 can be simultaneously controlled to superimpose a pulsatile flow component to the steady flow, thus allowing accurate measurement of pressure drop (with linear motor stopped) and having the valve opening/closing kinematics measured/evaluated in one single setup. It will reduce the extra steps tuning a pulsatile flow loop for faster and easier testing.

Principle of Operation

In FIG. 10 a simplified principle of flow schematic is illustrates. The circular loop on the upper right hand corner represents the pulse duplicator portion 110 as discussed above. In this pulse duplicator portion 110, a main loop of a main loop of fluid channel capable of providing a first flow path to a testing fluid is provided.

The main loop of fluid channel can include a section A 190, section B 191, and section C 192. There can be a first branch-off point 193 disposed on the main loop having a first branch channel 196 branching off and fluidly connecting the main loop to a three-way connection 199.

There can be a second branch-off point 194 disposed on the main loop having a second branch channel 197 branching off and fluidly connecting the main loop to the three-way connection 199.

There can be a third branch-off point 195 disposed on the main loop having a third branch channel 198 branching off and fluidly connecting the main loop to the three three-way connection 199.

As discussed above, the three-way connection 199 can be a three-way valve 160, where a user can control it so as to selectively shut off the first branch channel 196, the second branch channel 197, and the third branch channel 198. Alternatively, there is no three-way valve 160. Instead, the three-way connection 199 is a free-flowing connection, and there are individual mechanical valves disposed in the first branch channel 196, the second branch channel 197, and the third branch channel 198 so that the user may selectively shut off any of these channels by controlling its respective mechanical valve.

The steady-flow pump 152 as discussed above is shown in FIG. 10 to be disposed on the first branch channel 196.

While the second branch-off point 194 is directly connected to the third branch-off point 195 via section A of the main loop, the second branch-off point 194 is directly connected to the first branch-off point 193 via a section B of the main loop. In this embodiment, the compliance module 140 is fluidly connected to section A 190. The reservoir 144 is fluidly connected to section C 192. The linear motor 112 is fluidly connected to section A 190.

The valve testing unit 120 as discussed above can be fluidly disposed in section A 190 of the main loop to hold the prosthetic heart valve in a flow path of the main loop.

Comparable to FIGS. 5-9, the orifice one 154 would be disposed in the third branch channel 198 (not shown in FIG. 10). Similarly, orifice two 156 is disposed in the second branch channel 197.

In the simplified schematic of FIG. 10, the various testing modes as discussed above in FIG. 6-9 essentially requires a user to control a direction of fluid flow through the three-way connection by shutting off at least one of the first branch channel 196, the second branch channel 197, and the third branch channel 198.

Similar to the embodiment shown in FIG. 6, to perform a steady forward flow test, the user must turn on the steady flow pump 152 and shutting off the fluid flow in the second branch channel 197, and shutting off the fluid flow in section C 192 by way of a mechanical valve. Shutting off fluid flow in the second branch channel 197 can be accomplished by using a mechanical value or by using a three-way valve disposed at the three-way connection. The linear motor 112 is off.

To achieve a steady backward flow test, a user must turn on the steady flow pump 152 and shut off the fluid flow in the third branch channel 198, and shut off the fluid flow in section B 191. The linear motor 112 is off.

In order to achieve a pulsatile test, the user can simply shut off steady flow pump 152, turn on linear motor 112, and shut off fluid flow in at least two of the following branches: first branch channel 196, second branch channel 197, and third branch channel 198. By doing so fluid is prevented from flowing through the pump and orifice loop 150, and would instead remain in the pulse duplicator portion 110, which is the main loop as defined by section A 190, section B 191, and section C 192.

As discussed above, a user may use linear motor 112 to superimpose a pulsatile component during a steady forward flow test set-up to achieve a hybrid mode.

In one embodiment, the first branch-off point 193 only has three channels fluidly connected there to. In another embodiment, the second branch-off point 194 only has three channels fluidly connected there to. In still another embodiment, the third branch-off point 195 only has three channels fluidly connected there to.

The term "circuit of channels" is used to describe the entire circuitry in tester 100, such as all that is shown in FIGS. 5-10. Optionally, there may be one or more one-way valves (not the one being tested) disposed within the circuit of channels to help guide an intended direction of fluid flow. In one embodiment, such one-way valve can be disposed in section A 190. In another embodiment, such one-way valve can be disposed in section B 191. In yet one other embodiment, such one-way valve can be disposed in section C 192. In other embodiments, there can be no one-way valve anywhere in the circuit of channels except the one valve that is being tested.

Optionally, there may be one or more mechanical shut-off valves (not the one being tested) disposed within the circuit of channels to help effectuate shutting off the flow through a particular channel. In one embodiment, such mechanical shut-off valve can be disposed in section A 190. In another embodiment, such mechanical shut-off valve can be disposed in section B 191. In yet one other embodiment, such mechanical shut-off valve can be disposed in section C 192. In yet one other embodiment, such mechanical shut-off valve can be disposed in first branch channel 196. In still another embodiment, such mechanical shut-off valve can be disposed in second branch channel 197. In one other embodiment, such mechanical shut-off valve can be disposed in third branch channel 198. In other embodiments, there can be no mechanical shut-off valve anywhere in the circuit of channels except a three-way valve 160.

In one embodiment, the first branch channel 196 is a single-channel conduit and does not branch off between the first branch-off point 193 and the three-way connection 199. In another embodiment, the second branch channel 197 is a single-channel conduit and does not branch off between the second branch-off point 194 and the three-way connection 199. In still yet another embodiment, the third branch channel 198 is a single-channel conduit and does not branch off between the third branch-off point 195 and the three-way connection 199.

There is also contemplated an electronic and control system to control the tester 100. The whole fluidic system can be controlled and relevant data collected by a multi-function data acquisition card through a computer interface. The control system can adjust the flow resistance during any of the modes, such as the pulsatile flow testing mode.

The specification has set out a number of specific exemplary embodiments, but those skilled in the art will understand that variations in these embodiments will naturally occur in the course of embodying the subject matter of the disclosure in specific implementations and environments. It will further be understood that such variation and others as well, fall within the scope of the disclosure. Neither those possible variations nor the specific examples set above are set out to limit the scope of the disclosure. Rather, the scope of the present disclosure is defined solely by the claims set out below.

What is claimed is:

1. A multifunctional prosthetic heart valve tester having a circuit of fluid channels, the tester comprising:
    a main loop of fluid channel capable of providing a first flow path to a testing fluid;
    a first branch channel branching off at a first branch-off point located on the main loop wherein the first branch channel is fluidly connecting the main loop to a three-way connection;
    a second branch channel branching off at a second branch-off point located on the main loop wherein the second branch channel is fluidly connecting the main loop to the three-way connection;
    a third branch channel branching off at a third branch-off point located on the main loop wherein the third branch channel is fluidly connecting the main loop to the three-way connection;
    a steady-flow pump disposed on the first branch channel;
    wherein the second branch channel is directly connected to the third branch channel via a section A of the main loop, and the second branch channel is directly connected to the first branch channel via a section B of the main loop;
    a valve testing unit disposed on said section A of the main loop to hold said prosthetic heart valve in the first flow path.

2. The valve tester as recited in claim 1, wherein the three-way connection has a user-actuable three-way valve.

3. The valve tester as recited in claim 1, wherein a fluid flow in the first branch channel, in the second branch channel, and in the third branch channel can be selectively and individually shut.

4. The valve tester as recited in claim 3 further comprising a linear motor disposed on the main loop.

5. The valve tester as recited in claim 4 further comprising a first orifice disposed in the third branch channel.

6. The valve tester as recited in claim 4 further comprising a second orifice disposed in the second branch channel.

7. The valve tester as recited in claim 4 further comprising a flow resistance module fluidly connected to the circuit of fluid channels.

8. The valve tester as recited in claim 4 further comprising a compliance module fluidly connected to the circuit of fluid channels.

9. The valve tester as recited in claim 4 further comprising a fluid reservoir fluidly connected to the circuit of fluid channels.

10. A method of performing different types of testing on a prosthetic valve using a single tester having a circuit of channels, the method comprising:
    providing a main loop of fluid channel capable of providing a first flow path to a testing fluid;
    providing a first branch channel branching off at a first branch-off point located on the main loop wherein the first branch channel is fluidly connecting the main loop to a three-way connection;
    providing a second branch channel branching off at a second branch-off point located on the main loop wherein the second branch channel is fluidly connecting the main loop to the three-way connection;
    providing a third branch channel branching off at a third branch-off point located on the main loop wherein the third branch channel is fluidly connecting the main loop to the three-way connection;
    providing a steady-flow pump disposed on the first branch channel;
    wherein the second branch channel is directly connected to the third branch channel via a section A of the main loop, and the second branch channel is directly connected to the first branch channel via a section B of the main loop;
    wherein the first branch channel is directly connected to the branch channel via a section C of the main loop;
    placing said prosthetic heart valve in said section A of the first flow path;
    controlling a direction of fluid flow through the three-way connection by shutting off at least one of said first branch channel, said second branch channel, and said third branch channel.

11. The method as recited in claim 10 further comprising turning on the steady flow pump and shutting off the fluid flow in said second branch channel, and shutting off the fluid flow in said section C, to perform a steady forward flow test.

12. The method as recited in claim 11, wherein the shutting off of fluid flow in said second branch channel is done via a three-way valve disposed at the three-way connection.

13. The method as recited in claim 10 further comprising:
    turning on the steady flow pump;
    shutting off the fluid flow in said second branch channel;
    shutting off the fluid flow in said section C,
    using a linear motor fluidly connected to the circuit of channels to superimpose a pulsatile component to a steady forward flow.

14. The method as recited in claim 10 further comprising turning on the steady flow pump and shutting off the fluid flow in said third branch channel, and shutting off the fluid flow in said section B, to perform a steady backward flow test.

15. The method as recited in claim 10 further comprising:
    using a linear motor fluidly connected to the circuit of channels to impose a pulsatile component;
    shutting off the fluid flow in at least two of said first branch channel, said second branch channel, and said third branch channel, to perform a pulsatile flow test.

16. The method as recited in claim 15, wherein the at least two branch channels that are shut are said first branch channel and said second branch channel.

17. The method as recited in claim 16, wherein shutting off said first branch channel and said second branch channel is performed by using a three-way valve disposed at the three-way connection.

\* \* \* \* \*